US005799607A

United States Patent [19]
Greany et al.

[11] Patent Number: 5,799,607
[45] Date of Patent: Sep. 1, 1998

[54] CULTURE MEDIUM FOR PARASITIC AND PREDACEOUS INSECTS

[75] Inventors: Patrick D. Greany, Gainesville, Fla.; James E. Carpenter, Tifton, Ga.

[73] Assignee: The United States of America as represented by the Secretary of Agriculture, Washington, D.C.

[21] Appl. No.: 692,565

[22] Filed: Aug. 6, 1996

[51] Int. Cl.$^6$ .................................................. A01K 67/00
[52] U.S. Cl. .................................................. 119/6.5
[58] Field of Search .......................... 119/6.5, 6.6, 6.7, 119/6.8, 174; 426/2

[56] References Cited

U.S. PATENT DOCUMENTS

| | | | |
|---|---|---|---|
| 4,418,647 | 12/1983 | Hoffman . | |
| 4,820,529 | 4/1989 | Uchida et al. | 426/7 |
| 4,963,370 | 10/1990 | Uchida et al. | 426/7 |
| 5,134,125 | 7/1992 | Hara et al. | 514/19 |
| 5,492,899 | 2/1996 | Masor et al. | 514/47 |

OTHER PUBLICATIONS

Greany, P., *In Vitro Cell Dev. Biol.*, vol. 27A, p. 469 (1991).
Greany et al., *Bioscience*, vol. 34(11), pp. 690–696 (1984).
Greany et al., *Southwestern Entomologist*, Suppl. 12, pp. 89–94 (1989).
Greany, P., Abstract from the International Symposium on Molecular Insect Science, Oct. 22–27, 1989, Tuscon, Arizona.
Greany, P. *J. Insect Physiol.*, vol. 32(4), pp. 409–419 (1986).
Greany, P., *In Vitro*, vol. 17(3), p. 230 (1981).
Greany, P., *American Soc. Zool.*, vol. 20(4), p. 946 (1980).
Pennacchio et al., *Entomol. Exp. Appl.*, vol. 64, pp. 209–216 (1992).

Cohen et al., in: *Applications of Genetics to Arthropods of Biological Control Significance*, ed. Narang et al., publ. ©CRC Press, Chapter 7, pp. 122–132 (1994).
Cohen, A., *J. Econ. Ent.*, vol. 76(4), pp. 957–959 (1983).
Grenier et al., in: *Pest Management in the Subtropics*, ed. Rosen et al., pub. ©Interupt ltd., pp. 181–205 (1994).
Niijima, K., *Appl. Entomol. Zool.*, vol. 28(1), pp. 89–95 (1993).
Niijima, K., *Bull. Fac. Agric.*, Tamagawa Univ., No. 29, pp. 22–30 (1989).
Niijima, K., *Appl. Entomol. Zool.*, vol. 28(1), pp. 81–87 (1993).
Brower, J., *Advances in Parasitic Hymenoptera Res.*, pp. 535–546 (1988).
Cohen, A., *Southwestern Entomologist*, vol. 6(2), pp. 109–113 (1981).
Cohen, A., *J. Econ. Entomol.*, vol. 78, pp. 1173–1175 (1985).
Niijima t al., reprinted from: *FFTC Book Series No. 40*, "The Use of Natural Enemies to Control Agricultural Pests", pp. 191–198 (1990).
De Clercq et al., *Entomophaga*, vol. 37(1), pp. 149–157 (1992).
De Clercq et al., *Bioc. Sci. Tech.*, vol. 3, pp. 133–139 (1993).
De Clercq et al., *Proceedings of the 7th Workshop of the Global IOBC Working Group*: "Quality Control of Mass Reared Arthropods", Rimini (I), pp. 13–16 (Sep. 1993).

*Primary Examiner*—Thomas Price
*Attorney, Agent, or Firm*—M. Howard Silverstein; John Fado; Gail E. Poulos

[57] ABSTRACT

A variety of beneficial insects, from the egg stage to adult stage, have been successfully reared on a defined insect culture medium with a supplement containing poultry egg yolk, ground liver and glutamine. The medium contains no insect components. The medium is encapsulated to facilitate feeding and where applicable oviposition.

8 Claims, 8 Drawing Sheets

CULTURE MEDIUM FOR PARASITIC AND PREDACEOUS INSECTS

BACKGROUND OF THE INVENTION

1. Field of the Invention

The present invention relates generally to a culture media for rearing parasitic and predaceous insects and a method for culturing these insects for use in pest management systems.

2. Description of the Related Art

One of the greatest needs in the field of biological control is to be able to produce insect natural enemies such as predaceous and parasitic beneficial insects at a reasonable cost so that they can be used in lieu of conventional insecticides for pest control. In most systems, it is still necessary to rear beneficial insects by using their natural insect hosts/prey. Even when use is made of unnatural hosts, that serve adequately as laboratory hosts but are less expensive to obtain than the target host, it is generally too expensive to mass produce beneficial insects in sufficient numbers to enable augmentative releases (Grenier et al, In: Pest Management in the Subtropics(Rosen et al eds., 181–201, Intercept, Andover, 1994).

Simmonds (Bull. Entomolo. Res., Volume 35,219–226, 1944) attempted to culture three ectoparasitic ichneumonids of codling moth pupae on nutritive gelatine slants and raw beef Yazgan and House (Can. Entomol., Volume 102, 1304–1306, 1970) used a dietetic approach to prepare media utilizing existing knowledge of the nutritional requirements of insects generally, to successfully rear the parasitic hymenopteran *Itoplectis conquisitor* (Say) in chemically defined, synthetic diet. House (Can. Entomol., Volume 110, 331–333, 1978) encapsulated a synthetic diet within a Parafilm® capsule and created an artificial host that also served adequately for oviposition and rearing for *I. conquisitor*.

Hoffman and Ignoffo (Ann. Entomol. Soc. Amer., Volume 67, 524–525, 1974) and Hoffman et al (Ann. Entomol. Soc. Amer., Volume 68, 335–341, 1975) developed media that allowed at least partial success in rearing the pupal endoparasitoid, *Pteromalus puparum* L. and the egg parasitoid *Trichogramma pretiosum* (Riley), respectively. Another egg parasitoid, *Anastatus japonicus* Ashmead, is artificially mass reared in China (Li, In: *The Use of Natural Enemies to Control Agricultural Pests*, Proc. Intl. Seminar "The Use of Parasitoids and Predators to Control Agricultural Pests", 207–211, Food and Fertilizer Technology Center/ASPAC. Natl. Res. Ctr., MAFF, Japan, 1989). Two species of parasitic tachnid flies have been reared artificially, including *Eucelatoria bryani* Sabrosky (Nettles, Arch. Insect Biochem. Physiol., Volume 13, 167–175, 1990) and *Lixophaga diatraeae* (Towns) (Grenier et al, C.R. Acad. Sci. Paris D., Volume 387, 535–538, 1978).

Despite considerable effort, no hymenopterous larval endoparasitoid has been successfully reared from egg to adult in artificial media. However, partial success has been attained with two braconid larval endoparasitoids, *Microplitis croceipes* (Cresson) and *Cardiochiles nigriceps* Viereck, and one braconid larval-pupal endoparasitoid, *Diachasmimorpha* (=*Biosteres*) *longicaudata* Ashmead. It is believed that this type of parasitoid will be one of the most difficult to culture artificially because of the degree to which they are adapted to the endoparasitic way of life and their dependence upon a specialized environment (Greany, J. Insect Physiol, Volume 32, 409–419, 1986; Thompson Ann. Rev. Entomol., Volume 31, 197–219, 1986), even extending in some cases to a dependence upon host hormonal changes in order to molt (Lawrence, J. Insect Physiol., Volume 32, 295–298, 1986; In: Advances in Parasitic Hymenoptera Research (V. Gupta, ed.), 351–366, E. J. Brill, New York, 1988; Beckage, Exp. Parasitol., Volume 72, 332–338, 1991; Lawrence et al, (In: Parasites and Pathogens of Insects (S. N. Thompson, N. E. Beckage, and B. A. Federici, eds.)59–86, Academic Press, New York, 1993). This was shown by Lawrence (In Vitro Cell and Dev. Biol., Volume 27A, 487–4986, 1991) for *D. longicaudata*, which molts to the 2nd instar in vivo only at the larval-pupal molt of its tephritid fruit fly hosts, including the Caribbean fruit fly, *Anastrepha suspensa* (Loew). It was also shown that molting in vitro occurs only upon addition of 20–OH ecdysone.

The Heliothis/Heliocoverpa larval endoparasitoid *Microplitis croceipes* has been the subject of considerable attention by many investigators, primarily because of its potential value for biological control of these pest species (King et al, Southwestern Entomol., Volume 12, 1–9, 1989; King et al, Ann. Rev. Entomol., Volume 34, 53–75, 1990). The major impediment to increased use of this parasitoid is the cost of production using conventional (in vivo) rearing systems (Greany et al, Southwestern Entomol. Sup., Volume 12, 89–94, 1989). Efforts to rear *M.croceipes* in vitro have been only partially successful. Greany (J. Insect Physiol., Volume 32, 409–419, 1986) showed that egg development and hatch could occur in vitro, but was dependent upon a factor from host blood that probably derived from fat body. Greany et al (In: *Molecular Insect Science* (Hagedorn et al, eds.), 306, Plenum Press, New York and London, 1990) showed that this factor is a protein with a molecular weight of ca. 230 kilodaltons. Ferkovich et al (Arch. Insect Biochem. and Physiol., Volume 14, 111–120, 1990) showed that fat body coincubation with *M. croceipes* eggs stimulated protein biosynthesis in the eggs. They have also shown that a fat body-derived cell line could be used to condition media and enable development and hatch of *M croceipes eggs*. Larval development of croceipes in vitro was shown by Greany (1986, supra) to become arrested in the 1 st instar. Larvae removed from parasitized hosts after they are at least 3 mm in length in vivo, will molt in vitro without the addition of 20–OH ecdysone (Greany, unpublished).

Pennachio et al (Entomol. Exp. Appl., Volume 64, 209–216, 1992) have cultured the *Heliothis virescens* braconid larval endoparasitoid *Cardiochiles nigriceps* Viereck from post-germband eggs to the 2nd instar in an artificial medium comprised of an amino acid, salt, vitamin, and carbohydrate-containing medium supplemented with bovine serum albumin, enzymatically hydrolyzed lactalbumin, fetal bovine serum, egg yolk and milk. However, the larvae grew much slower than in vivo, only 10% molted to the 2nd instar and they did not complete development.

Niijima et al (Bulletin of the Faculty of Agriculture, Volume 29, 22–30, 1989;Niijima et al, In: The Use of Natural Enemies to Control Agricultural Pests, 190–198, 1990; Niijima, Appl. Entomol. Zool., Volume 28 (1), 81–87 and 89–94, 1993;) have developed chemically defined diets for rearing the predaceous insects such as *Chrysopa septempunctata, C. formosa, C. initima, C. perle, C. canea, C. furcifera,* and *M. formosanus*. Powdered honeybee drones and powdered aphids were the simplest diets. The chemically defined diets include up to 23 amino acids, 17 vitamins, 11 minerals, 5 organic acids, 4 fatty acids, 2 sugars, and cholesterol.

Cohen (The Southwestern Entomologist, Volume 6 (2), 109–113, 1981.; J. Econ. Entomol., Volume 78, 1173–1174, 1985) described several diets for rearing the predaceous insect *Geocoris punctipes*. The diets contain yeast hydrosylate, casein hydrosylate, cholesterol, sugars, agar, Wesson salts, potassium phosphate, magnesium chloride, streptomycin, auremycin, formalin, and Tween 80. In addition to these ingredients the diets included either corn oil, Vanderzant vitamin mix, lecithin, or phenylalanine and all were encapsulated. These diets supported between 14% and 59% success in development of 1st-stage nymphs to adults. Another diet consisted of a paste made up of ground beef liver and ground beef in equal amounts, and sucrose upon which 5 complete continuous generations have developed.

De Clercq et al ( Entomophaga, Volume 37(1), 149–157, 1992; Biocontrol Sci. And Tech., Volume 3, 133–139, 1993; Rimini (I), 13–16, 1993) disclose a meat diet that was sufficient to produce consecutive generations of predatory bugs of the genus Podisus which had viability and predatory performance similar to those bugs continuously fed on live prey. The diet consists of beef liver, fatty ground beef, sucrose, ascorbic acid, Wesson's salt mixture, and fresh hen's egg yolk which are blended into a paste and wrapped in parafilm.

There remains a need in the art for an effective medium and method for culturing predator and parasitoid beneficial insects from the egg stage to adult. The present invention described below provides a medium, completely devoid of insect components, which enables rearing of many different species of economically important predatory and parasitic beneficial insects which is different from prior art media.

SUMMARY OF THE INVENTION

It is therefore an object of the present invention to provide a medium for mass rearing of predator and parasitoid insects.

Another object of the present invention is to provide a medium for mass rearing of predator and parasitoid insects that is free of any insect components.

A still further object of the present invention is to provide a medium that has been supplemented for mass rearing of predator and parasitoid insects that includes approximately 13% protein, approximately 10% fat, approximately 6% carbohydrate and approximately 1% minerals when a supplement is added.

A further object of the present invention is to provide a medium for mass rearing of predator and parasitoid insects containing a supplement that includes poultry egg yolk and liver as sources of protein, fat and minerals.

Another object of the present invention is to provide a medium for mass rearing of predator and parasitoid insects wherein the medium is encapsulated to form a means for feeding and/or oviposition for the insects.

A still further object of the present invention is to provide a method for mass rearing of predator and parasitoid insects from the egg stage to the adult stage.

Further objects and advantages of the present invention will become apparent from the following description.

DETAILED DESCRIPTION OF THE INVENTION

Mass rearing of beneficial insects as biocontrol agents is important given the concerns about the use of chemical insecticides which create, for example, insecticide residues on commodities, resistance of insects to chemical insecticides, hazardous exposure to pesticide applicators, environmental contamination and destruction of natural biocontrol agents such as beneficial insects. Furthermore, as pests become more resistant to pesticides, more frequent treatments are required which increases the human health hazard.

An alternative to chemical pesticides is the use of biocontrol agents such as beneficial insects which include predaceous and parasitic insects which kill harmful pests. The development of artificial diets and in vitro rearing procedures is important to enable the use of beneficial insects in pest management. This use could have tremendous economic and environmental impact. For example, for one commodity, cotton, the total cost for arthropod pests, including control costs plus losses, is on the order of approximately $685 million annually.

A supplement for insect culture media containing effective amounts of glutamine, poultry egg yolk and liver, in order to culture parasitic and predaceous insects from eggs to adult, has been discovered. The supplemented medium contains no additional insect components, such as for example, insect hormones, hemolymph or substances derived from media removed from cultured insect cell lines.

The medium of this invention is applicable to any insect, particularly beneficial insects such as predaceous and parasitic insects. Such insects include, but are not limited to, insects from the orders Hemiptera, Hymenoptera, Coleoptera, Diptera, Heteroptera and Neuroptera. Examples of specific insects are *Geocoris punctipes, Podisus maculiventris, Perillus bioculatus, Lyctocoris campestris* and *Xylocoris flavipes*, all hemipterans; *Calosoma sycophanta* and *Colemegilla maculata*; coleopterans; and *Diapetimorpha introita* and *Cryptus albitarsus*; hymenopterans.

The term supplement means any supplement for insect culture media which enables an adult insect to develop from an egg without the addition of other insect components. The components of the supplement include glutamine, ground liver and fresh poultry egg yolk. The components are in amounts effective to rear insects from the egg to adult when it is added to a defined insect culture medium. The ground liver is derived from fresh whole livers which are preferably bovine, porcine or ovine livers, most preferably bovine liver. The fresh poultry egg yolk is derived from, for example, fresh eggs of chicken, turkey, duck, goose, quail, ostrich, or pheasant eggs, most preferably chicken eggs. As used herein, "in amounts effective", "an effective amount" or "an amount effective", refer to the amount of supplement added to a defined insect culture media in order to rear insects from the egg to adult. As used herein, a defined culture medium is a medium of known components. The term complete medium is a defined medium containing the supplement of the present invention.

The complete insect culture medium has a composition of approximately 4–8% by weight of carbohydrate, approximately 10–15% by weight protein, approximately 8–13% by weight fat, approximately 0.5–2% by weight minerals and approximately 62–78% by weight water when the above described supplement is added to the medium. The preferred composition is approximately 6% by weight carbohydrate, approximately 13% by weight protein, approximately 10% by weight fat, approximately 1% by weight minerals and approximately 70% by weight water. Examples of defined media useful in the present invention include SF-900II and IPL-41 (GIBCO-BRL Life Technologies, Inc., 8451 Helgerman Court, P.O. Box 6009, Gaithersburg, Md. 20884-9980). The carbohydrate component is derived from a combination of the basal culture medium plus the supplemental liver and egg yolk. Fresh chicken egg yolk contains approximately 0.31 grams per 100 grams and fresh beef liver contains approximately 1.65 grams per 100 grams. The protein component is derived from a combination of the basal culture medium plus the supplemental liver and egg yolk. Fresh chicken egg yolk has a protein content of approximately 16.1 grams per 100 grams and fresh beef liver has a protein content of approximately 19.7 grams per 100 grams. The fat component is entirely derived from the liver and egg yolk supplements. Fresh chicken egg yolk has approximately 31.9 grams per 100 grams and fresh beef liver has approximately 3.1 grams per 100 grams. The mineral content is derived from the basal culture medium, the egg yolk and the liver, plus a minor amount of sodium and potassium added during the adjustment of pH by way of adding sodium hydroxide and potassium hydroxide. Fresh chicken egg yolk has a mineral content of 1.7 grams/100 grams and fresh beef liver has a mineral content of 1.4 grams per 100 grams.

The supplement is prepared and added to the defined insect culture medium during media preparation using conventional techniques. The components of the supplement are dissolved or suspended in water, more preferably sterile distilled water, most preferably sterile double deionized water. The pH of the complete medium is preferably corrected to fall within a range of approximately 5.0–8.5, more preferably 6.4–7.0, most preferably 6.8.

In the methods according to the present invention, the medium is prepared, as described above, and encapsulated by dispensing aliquots of medium into wells made by vacuum formation of sheets of membranous polymeric material, such as polymeric film formers, using an aluminum template with suitably-sized holes over a plenum (a void volume), to which a regulated vacuum is applied. The template is a machined piece of any suitable material, generally aluminum. The template can be any suitable size; this is dependent on the number of capsules that are to be prepared at one time. To prepare capsules for the following examples the template was approximately 3.5"×5"×0.75" thick. Holes of approximately 1.5 mm to approximately 1.0 cm in diameter are drilled into the template. The hole size used determines the volume of each encapsulated unit. One of ordinary skill in the art can readily determine the size needed dependent on the size of the insects which will be fed. All holes are drilled completely through the template to allow an applied vacuum to be exerted on the membrane that is located on the surface of the template. The patterns for the holes in the template can be coincident with the well patterns for standard tissue culture plates or ELISA plates for ease of culturing the insects. The plenum is also a machined piece of any suitable material, generally aluminum. It is of the same dimensions of the template and is milled so as to be mostly a void volume with approximately $\frac{3}{16}$" walls and approximately $\frac{3}{16}$" bottom. A gasket is sandwiched between the template and the plenum. A hose barb is attached to a tapped hole through one end of the bottom of the plenum for attachment of a vacuum line. The membrane should have a combination of thickness, stretch and hardness such that it will retain its shape and will also be penetrable by the insects. Common polymeric film formers such as polyethylene, polypropylene, polyvinyl chloride, PARAFILM® and the like are illustrative of suitable materials, although determination of others meeting the aforementioned criteria would be within the ambit of the skilled artisan. It is preferable that the membrane is permeable to oxygen and carbon dioxide but not to water vapor when insects are cultured which oviposit in the capsules. After dispensing the medium, a backing of any of the above mentioned polymeric films is applied and sealed, using a means for applying heat, such as, for example, a heated roller. The capsules are then sterilized using gamma radiation using a typical dose of approximately 500 KR. At least a single capsule is put into a tissue culture well containing one parasitoid larvae. Predators are usually reared in groups using multiple capsules. Predators can be reared individually using at least one capsule per predator. The ambient rearing conditions are approximately 14 hours light, approximately 10 hours dark, approximately 60–80% relative humidity at approximately 26°–30° C. The shelf life of the diet-containing capsules is at least about 2–4 months at about 4° C.

The following examples are intended only to further illustrate the invention and are not intended to limit the scope of the invention as defined by the claims.

EXAMPLE 1

*Diapetamorpha introita* (Hymenoptera:Ichaeumonidae) is a native North American ectoparasitoid of *Spodoptera* species which are major pests of agricultural crops. Female *D. introita* wasps search the soil surface until they find a host pupation site. When they have determined the boundaries of the pupation site, they insert their ovipositor through the soil cap covering the pupal gallery and lay an egg. After the larva hatches from the egg, it locates the host pupa and begins to feed on the host pupa. Within about five days the larva will have consumed the entire content of the host pupa.

*Podisus maculiventris* is a polyphagous predatory stinkbug that attacks a wide variety of prey species, including eggs and larvae, mainly in Lepidoptera and Coleoptera. Females can produce up to 500 eggs and live up to 125 days. They typically consume about 1 prey individual every 2 days in nature. Development (egg-adult) generally takes about 25–30 days at 26° C. It is native to North America and is found from Quebec to Florida, and from New England to the Pacific. It has been mass-cultured using natural prey for release against the Colorado potato beetle in the U.S. and Europe.

The colony of *Diapetamorpha introita* originated by field collection in the vicinity of Tifton, Ga. It was collected by holding parasitized Spodoptera pupae in the laboratory until emergence of adult wasps. Thereafter, a colony has been maintained at the USDA ARS Insect Biology & Management Laboratory in Tifton, by using laboratory-reared *Spodoptera frugiperda* pupae as hosts. For each generation, *D. introita* wasps are provided with *S. frugiperda* pupae in soil. The female wasps search for the pupae and oviposit into the cell within the soil that contains the host pupa. The parasitoid egg ultimately hatches and the neonate larva begins to feed upon the pupa as an ectoparasitoid (i.e., externally). The larva may eventually penetrate the cuticle of the dead host and feed upon its tissues. The behavior of *D. introita* larvae on the artificial diet capsules is similar to that on natural hosts.

The colony of *Podisus maculiventris* is maintained at the USDA ARS Center for Medical, Agricultural, and Veterinary Entomology Research Laboratory in Gainesville, Fla. It originated from a colony maintained at the USDA ARS Chemical Ecology Research Laboratory in Beltsville, Md. The original source material was obtained through field collection. The colony is maintained by using natural prey, generally Plodia eggs and larvae, and larvae of the fall armyworm and/or beet armyworm. This predator is reared conventionally by placing prey such as moth eggs and later, larvae, in a cage for consumption by the predator nymphs and adults. Typically, netting is provided as a means of increasing surface area available within the cage in order to minimize contact among the predator individuals. Supplemental water in routinely provided.

EXAMPLE 2

Encapsulation of the medium is accomplished by stretching PARAFILM® uni- or bidirectionally and applying to the template described above. A slight negative pressure, approximately minus 2 inches of mercury, is applied to the membrane and a probe of a diameter slightly less than that of the holes in the template is used to deform the membrane until it has been maximally stretched to a final thickness of approximately 10–15 microns. The medium is injected into each concavity in the template. A plastic film, such as for example, Handiwrap®, is then applied to the surface of the template. A piece of aluminum foil is then applied over the plastic wrap and a heated roller (approximately 170° C.) is used to heat seal the PARAFILM® to the plastic wrap. The aluminum foil does not fuse to the wrap. At least one pass of the roller in each direction is all that is required to achieve an adequate seal.

EXAMPLE 3

The medium-containing capsules, as prepared above in Example 2, are placed either individually in a culture dish or by providing multiple capsules in a cage. Highly cannibalistic species of predators or parasitoids are cultured individually. *D. introita* larvae are placed in the culture dish or cage containing the diet capsule(s) are reared using a typical light/dark cycle of approximately 14 hours light, approximately 10 hours dark, approximately 60–80% relative humidity and approximately 26°–30° C. Supplemental water is routinely provided.

Figure 1:
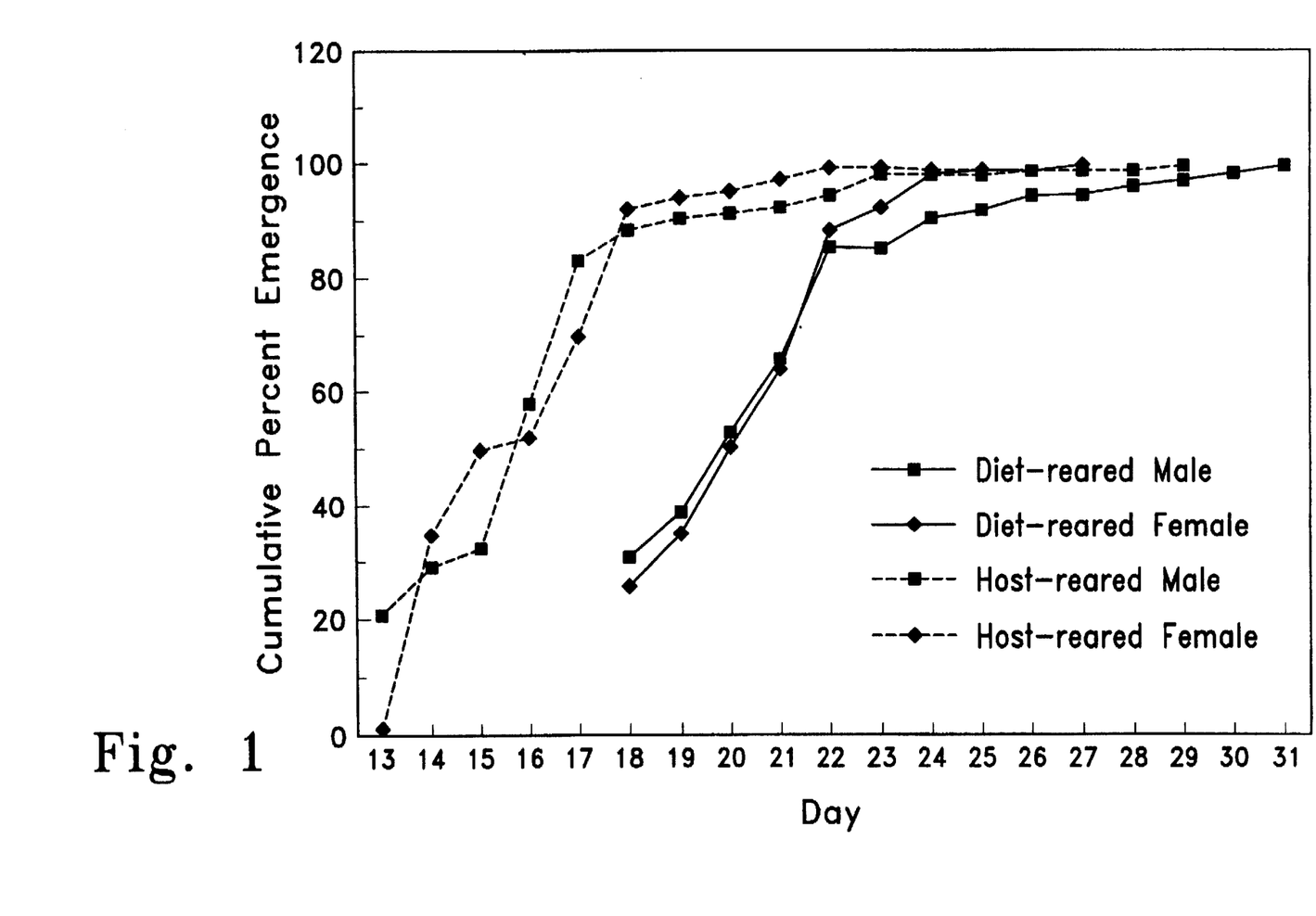
FIG. 1 is a graph comparing cumulative percent emergence of diet-reared and host-reared male and female *Diapetamorpha introita*.
Figure 2:
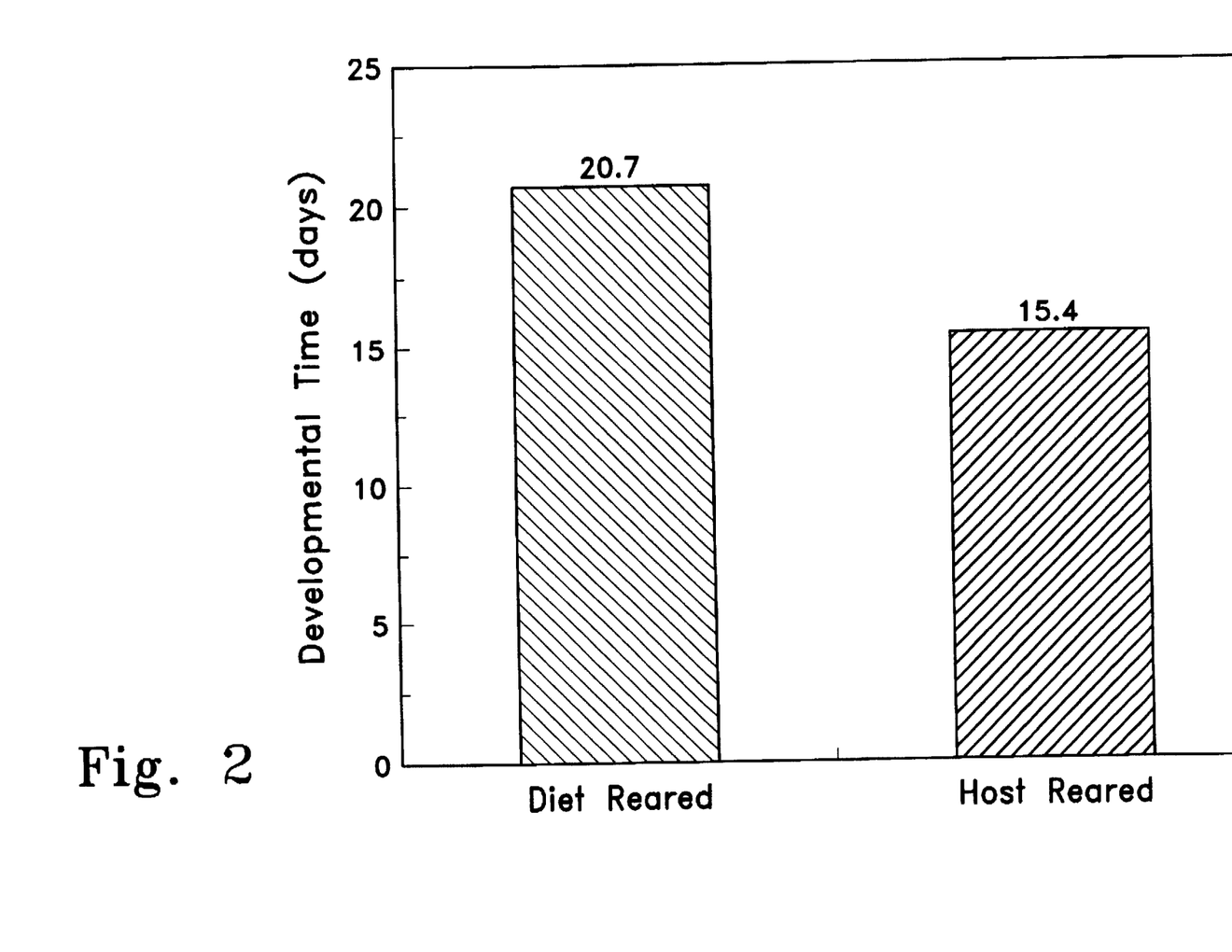
FIG. 2 is a bar graph showing developmental time of diet-reared and host-reared *Diapetamorpha introita*.
Figure 3:
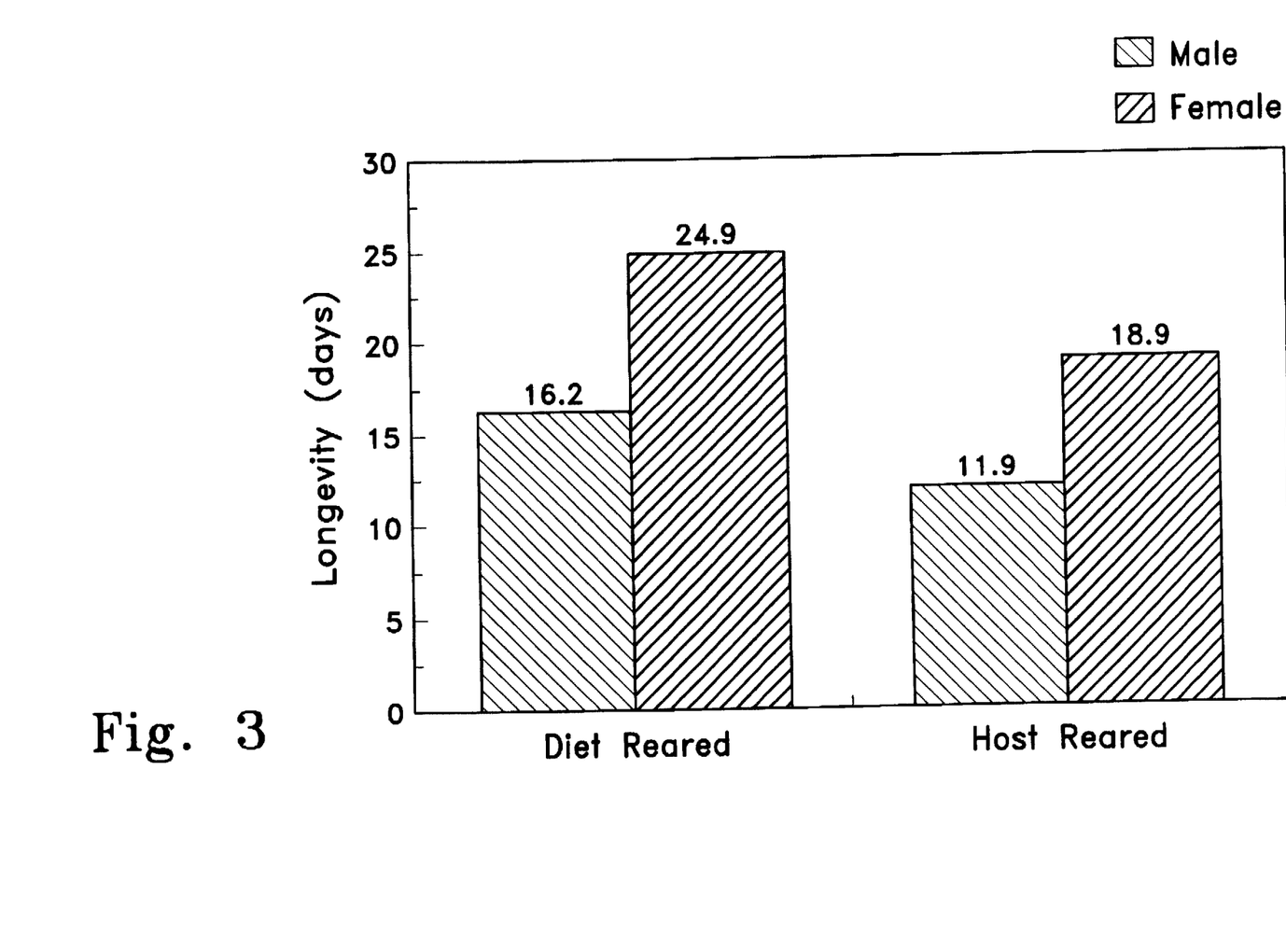
FIG. 3 is bar graph showing longevity of diet-reared and host-reared male and female *Diapetamorpha introita*.
Figure 4:
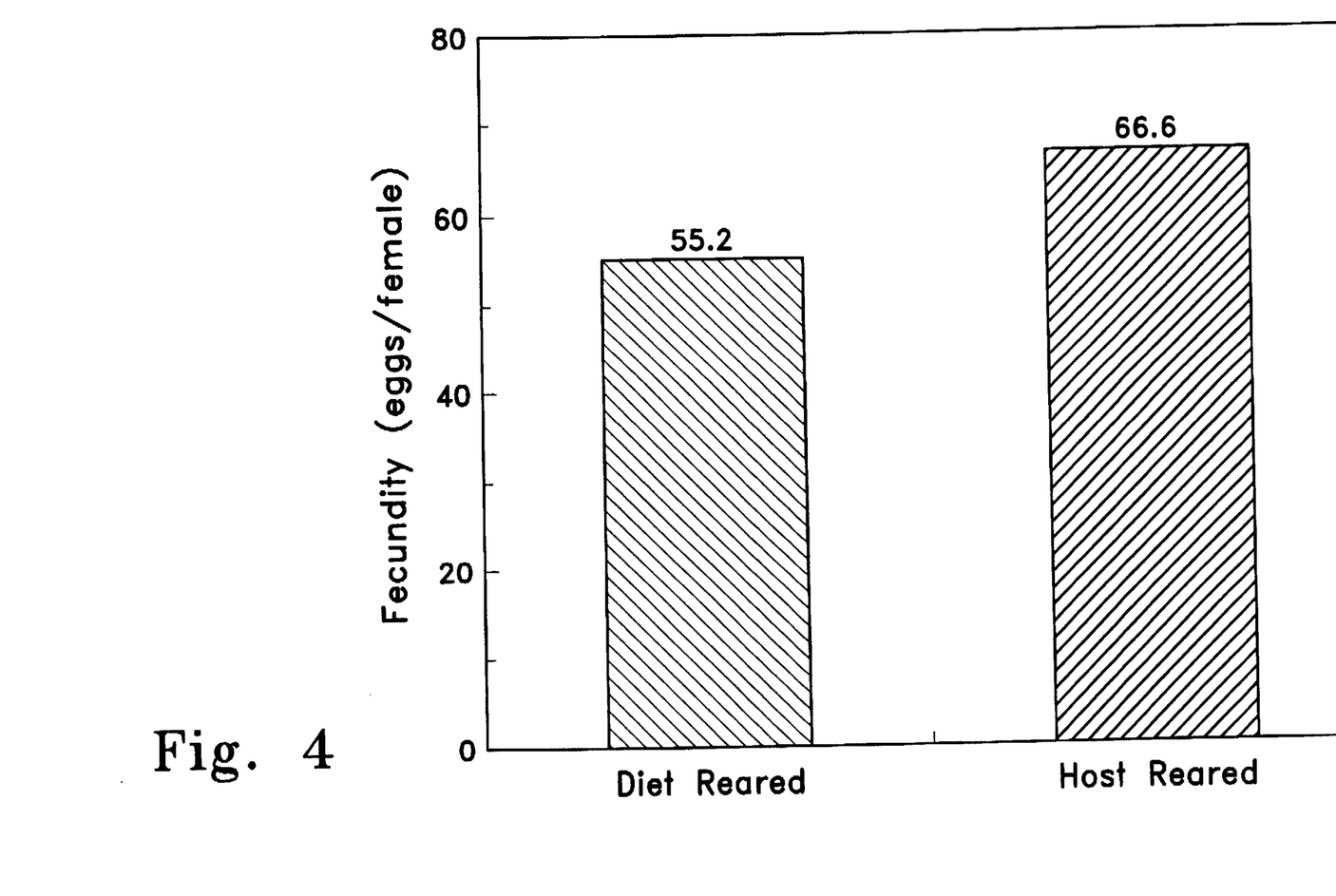
FIG. 4 is a bar graph showing fecundity of diet-reared and host-reared female *Diapetamorpha introita*.
Figure 5:
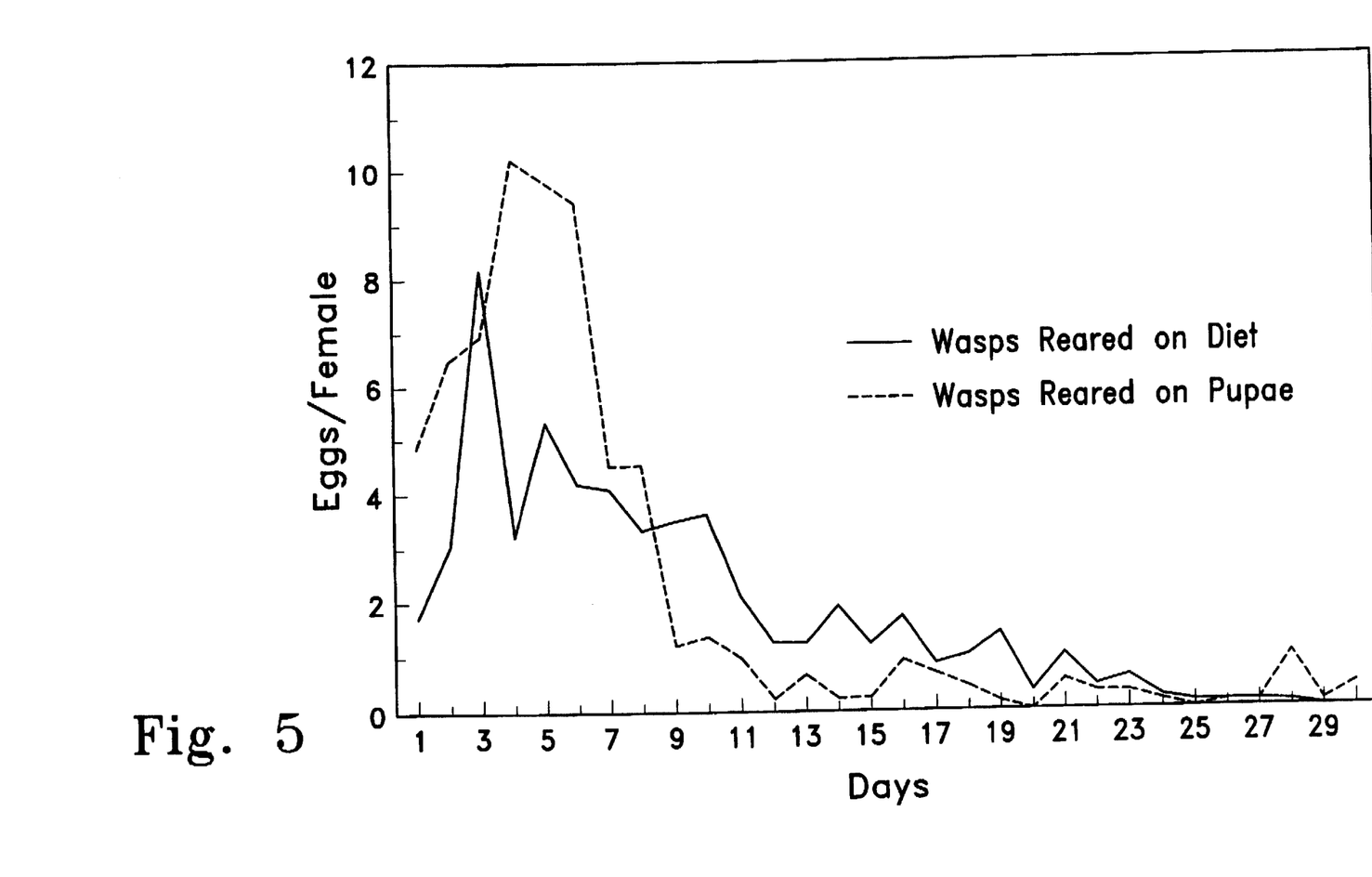
FIG. 5 is a graph showing mean oviposition/day for diet-reared and host-reared *Diapetamorpha introita*.
Figure 6:
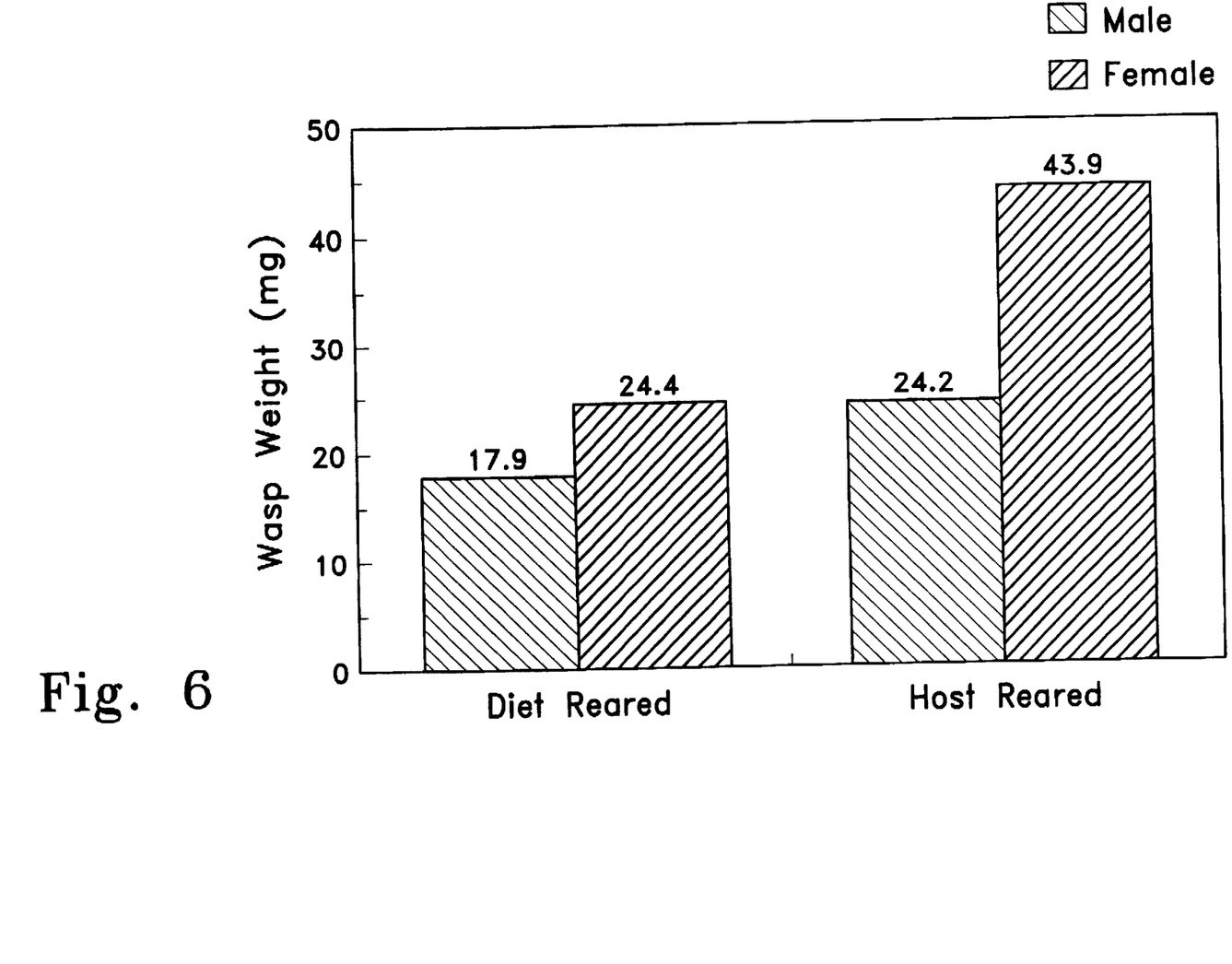
FIG. 6 is a bar graph showing mean weight of diet-reared and host-reared male and female *Diapetamorpha introita*.

The emergence pattern is similar for diet-reared and host-reared *D. introita* (FIG. 1). However, there is a significant delay in the developmental time of diet-reared wasps (FIG. 2). There is no significant difference between the longevity of diet-reared and host-reared *D. introita* (FIG. 3). The mean number of eggs laid per female is significantly less for diet-reared wasps than for host-reared wasps (FIG. 4). The difference in oviposition is greatest on the 4th, 5th and 6th day after emergence (FIG. 5). The mean weight of wasps reared on the diet of the instant invention is significantly less than the mean weight of wasps reared on hosts (FIG. 6).

EXAMPLE 4

Figure 7:
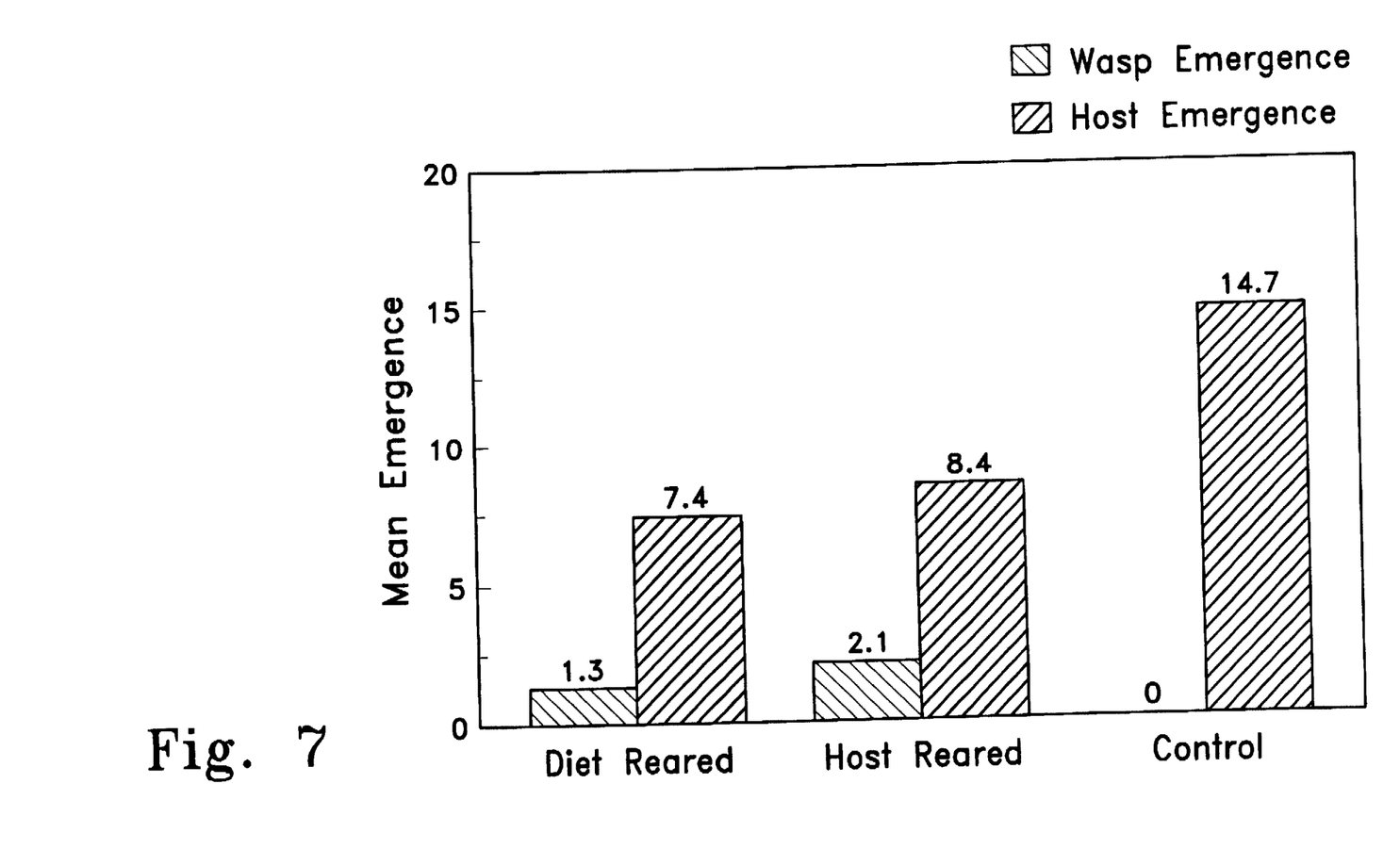
FIG. 7 is a bar graph showing mean emergence of diet-reared and host-reared *Diapetamorpha introita* and host, *Spodoptera frugiperda*, after introduction of *D. introita* into cages containing host infested whorl-stage corn.

Thirty field cages containing whorl-stage corn (14 plants/cage) were infested with 4th instar *Spodoptera frugiperda* (host) (3 larvae/plant). After *S. frugiperda* pupation, 4 pairs of diet-reared *D. introita* were released in each of ten cages, 4 pairs of host-reared *D. introita* were released in each of ten cages and the remaining ten cages were control. The experimental design was a randomized complete block. Cages were inspected daily and all emerging adults recorded. The mean number of emerging hosts (*S. frugiperda*) was significantly reduced in cages where *D. introita* wasps had been released (FIG. 7). The emergence means of wasps and hosts in cages where diet-reared wasps had been released were not significantly different from the emergence means of wasps and hosts in cages where host-reared wasps had been released. The diet-reared wasps demonstrate a propensity to search for and attack natural hosts in field cage trials.

EXAMPLE 5

Figure 8:
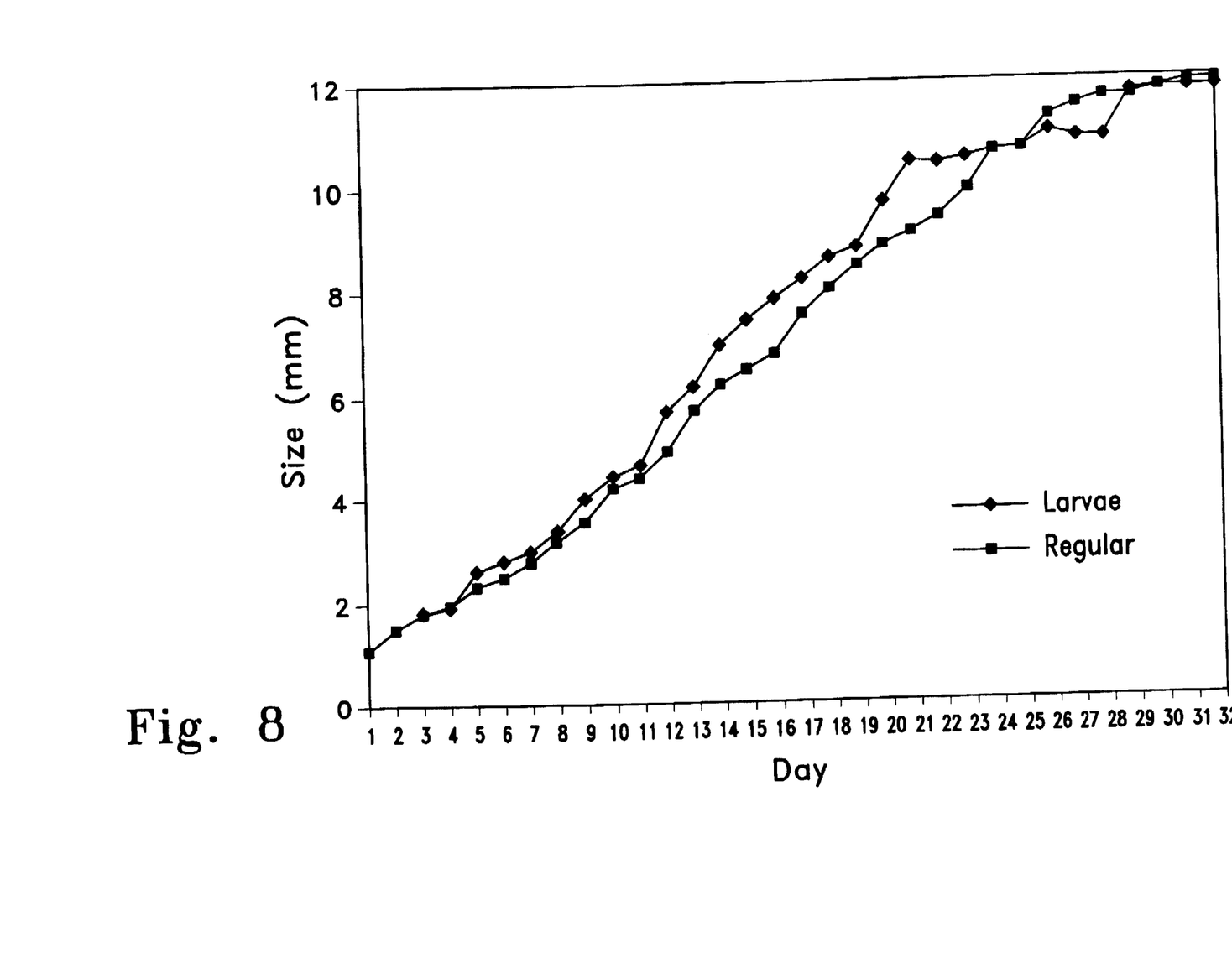
FIG. 8 is a graph comparing sizes of diet-reared and host-reared *Podisus maculiventris* during growth up to the adult stage.

*P. maculiventris* larvae are placed in a cage containing the diet capsule(s) and are reared using a typical light/dark cycle of approximately 14 hours light, approximately 10 hours dark, approximately 60–80% relative humidity and approximately 26°–30° C. Supplemental water is routinely provide. Typically, netting of some sort is provided as a means of increasing the surface area available within the cage, in order to minimize contact among the predator individuals. The diet-reared adult *P. maculiventris* grow to the same size as those reared on Plodia larvae (FIG. 8).

EXAMPLE 6

Table 1 below describes the use of the diet of the present invention for rearing other selected species of parasitoids and predators as described in Examples 3 and 5 above.

The foregoing detailed description is for the purpose of illustration. Such detail is solely for that purpose and those skilled in the art can make variations therein without departing from the spirit and scope of the invention.

TABLE ONE

| Use of artificial diet ("DI-Diet") for rearing selected species of parasitoids and predators. | | | | | | | |
|---|---|---|---|---|---|---|---|
| | | | | Reared | Fecundity evaluated | | |
| | Commercially | Parasitoid/ | Usual | egg to | | | $P_1$ egg |
| Species | available? | predator | host/prey | adult | Lab | Field* | viability |
| *Cryptus albitarsus* | no | ectoparasitoid | Heliothis & Helicoverpa spp. | yes | no | no | n/t** |
| *Calosoma* | no | predator | gypsy moth, | yes | yes | no | n/t |

TABLE ONE-continued

Use of artificial diet ("DI-Diet") for rearing selected species of parasitoids and predators.

| Species | Commercially available? | Parasitoid/ predator | Usual host/prey | Reared egg to adult | Fecundity evaluated Lab | Fecundity evaluated Field* | $P_1$ egg viability |
|---|---|---|---|---|---|---|---|
| sycophanta | | | brown tail moth | | | | |
| Coleomegilla maculata | yes | predator | miites, small insects | no | no | no | n/t |
| Perillus bioculatus | no | predator | Colorado potato beetle | yes | no | no | n/t |
| Xylocoris flavipes/ Lyctoris campestris | yes/no | predator | stored products insects | yes | no | no | n/t |
| Geocoris punctipes | no | predator | mites, small insects | yes | no | no | n/t |

*Field cage trials.
**Not tested.

We claim:

1. A medium suitable for the culture of beneficial insects comprising a supplement containing ground liver, poultry egg yolk and glutamine.

2. The medium of claim 1 wherein said medium is a defined medium.

3. The medium of claim 1 wherein the liver is bovine, porcine, or ovine.

4. The medium of claim 3 wherein the liver is bovine.

5. The medium of claim 1 wherein the egg yolk is chicken, turkey, duck, goose, quail, ostrich, or pheasant.

6. The medium of claim 5 wherein the egg yolk is chicken.

7. The medium of claim 1 wherein the composition of the medium with supplement is approximately 4–8% by weight carbohydrate, approximately 10–15% by weight protein, approximately 8–13% by weight fat, approximately 0.5–2% by weight minerals and approximately 62–78% by weight water.

8. A method for rearing insects from an egg to adult comprising providing an encapsulated defined insect culture medium containing a supplement containing ground liver, poultry egg yolk and glutamine, and culturing said insects with said encapsulated medium.

* * * * *